United States Patent [19]

Kiener et al.

[11] Patent Number: 5,254,533
[45] Date of Patent: Oct. 19, 1993

[54] ELFAMYCIN

[75] Inventors: Thierry Kiener, Neris les Bains; Arie Kies, Commentry; Rodolphe Margraff, Viry-Chatillon, all of France

[73] Assignee: Rhone-Poulenc Rorer S.A., Antony, France

[21] Appl. No.: 652,109

[22] Filed: Feb. 8, 1991

[30] Foreign Application Priority Data

Feb. 8, 1990 [FR] France .................. 90 01442

[51] Int. Cl.$^5$ ............................................. C07H 17/02
[52] U.S. Cl. ............................................ 514/8; 514/2; 536/53; 536/17.2; 536/17.4; 536/18.2; 435/105
[58] Field of Search ............... 536/53, 17.2, 17.4, 536/18.2; 514/8, 2

[56] References Cited

U.S. PATENT DOCUMENTS

| | | | |
|---|---|---|---|
| 4,112,216 | 9/1978 | Maehr | 536/1.1 |
| 4,218,560 | 8/1980 | Maehr | 536/1.1 |
| 4,336,250 | 6/1982 | Scheifinger | 424/115 |

OTHER PUBLICATIONS

Maehr, Chemical Abstracts, vol. 95(7), #62607y, Aug. 17, 1981.
Maehr et al., Chemical Abstracts, vol. 81(7), #37143x, Aug. 19, 1974.
Yarwood et al., Chemical Abstracts, vol. 100(5), Jan. 30, 1984, #33501a.
Hoffman-La Roche, Chemical Abstracts, vol. 89(15), Oct. 9, 1978, #129884k.
Chinali, Chemical Abstracts, vol. 96(11), Mar. 15, 1982, #85296f.
Chinali, Chemical Abstracts, vol. 95(23), Dec. 7, 1981, #198105r.
Dolle et al., J. Am. Chem. Soc., vol. 107, pp. 1695–1698.
Kempf et al., J. Antibiotics, vol. 39(10), 1986, pp. 1361–1367.
Carter et al., J. Antibiotics, vol. 41(10), 1988, pp. 1511–1514.

Primary Examiner—Ronald W. Griffin
Assistant Examiner—Pamela S. Webber
Attorney, Agent, or Firm—Finnegan, Henderson, Farabow, Garrett & Dunner

[57] ABSTRACT

A compound of the elfamycin family, a process for preparing it and its use in the feeding of monogastric animals.

3 Claims, No Drawings

ELFAMYCIN

The present invention relates to a new compound of the elfamycin family, to a process for the preparation of this new compound and to a method of use therefore.

Elfamycins are antibiotics which have long been recognized for use in the treatment of human and animal infections.

Elfamycins generally correspond to the following general formula:

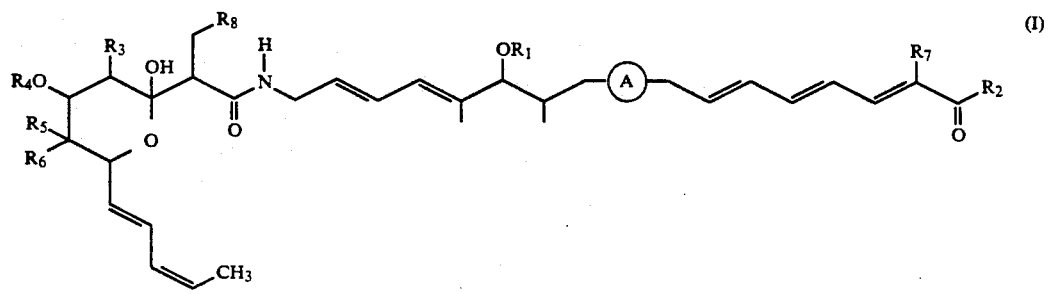

in which:
- the group $R_1$ represents an alkyl unit,
- the group $R_2$ represents a hydroxyl group or a substituted pyridone radical,
- the groups $R_3$, $R_5$, $R_6$ and $R_7$ represent either methyl or hydroxyl groups, or hydrogen, or alkyl groups,
- the group $R_4$ represents an alkyl group, hydrogen or a glycosidyl group,
- the group $R_8$ represents a hydrogen atom, a methyl group or an O(diginose)$_2$ group, and
- the group A represents a dihydroxyethanediyl link or a mono-or dihydroxyfuran ring in the 2,5-position of the furan ring.

For the purposes of the present invention a pyridone group is defined as:

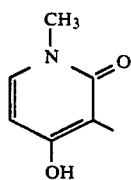

The prior art elfamycins may be divided into 3 classes according to the nature of the radicals $R_2$ and $R_4$.

The first class is limited to the compounds of the formula (I) for which $R_2$=OH and A represents a hydroxyfuran group.

In this class, U.S. Pat. No. 4,476,139 describes compounds of formula (I) for $R_1$=CH$_3$, $R_2$=OH, $R_3$=$R_4$=$R_7$=$R_8$=H, $R_5$=CH$_3$, and $R_6$=OH and U.S. Pat. Nos. 4,705,688 and 4,753,798 describe compounds of the formula (I) for $R_1$=CH$_3$, $R_2$=OH, $R_3$=OCOCH$_2$C$_6$H$_5$ or OH, $R_4$=H or COCH$_2$C$_6$H$_5$, $R_5$=$R_6$=CH$_3$, $R_5$=$R_6$=CH$_3$, $R_7$=H, and $R_8$=—O(-diginose)$_2$. These compounds exhibit considerable antibiotic activity with respect to a large number of microorganisms including Bacillus, Proteus, Staphylococcus, Brucella, *Escherichia coli*, Pseudomonas,.Enterobacter, and Streptococcus. These elfamycins are used to combat infections which are sensitive to them, but they can also be used as an agent to promote the growth of monogastric animals.

The second class of elfamycins includes compounds of the formula (I) for which $R_2$ represents a pyridone group. In this class, U.S. Pat. No. 3,708,577, describes the use of these elfamycins as agents promoting animal growth. This class of elfamycins substituted with a pyridone group, which pyridone group may itself be substituted, include those sold under the names Efrotomycin, Aurodox, Kirromycin and Heneicomycin. (See MAEHR, H; M. LEACH; T. H. WILLIAMS & J. F. BLOUNT; The Chemistry of Aurodox and related antibiotics, Can. J. Chem. 58, 502-526, 1980). This class of elfamycins also exhibits an antibiotic effect on a large number of microorganisms and is useful in the promotion of animal growth. However, the presence of the pyridone group makes the extraction of this class of elfamycins from fermentation media harder and diminishes their stability in the presence of moisture and heat.

A third class of elfamycins includes compounds of formula (I) in which the group $R_4$ represents a polyglycidyl unit. These elfamycins are exemplified in U.S. Pat. Nos. 4,497,969 and 4,024,251.

These elfamycins exhibit, like those mentioned above, an antibiotic effect and an effect on animal growth. Some compounds of this class are produced in the form of two isomers which are difficult to separate.

Until the present time, it has appeared necessary to use antibiotics having a broad spectrum of activity to promote animal growth. Antibiotics having this broad spectrum of activity have been prepared using processes affording low productivity and requiring cumbersome extraction techniques. Additionally, some of these compounds, particularly those of the second and third classes, exhibit insufficient stability in the presence of heat to permit their incorporation into granules for use in animal feeds. The formation of granules for use in animal feed is performed by heating under pressure as described in U.S. Pat. No. 4,597,969.

The animal feed industry has continued looking for a compound which will promote animal growth, which is also easy to produce by fermentation processes, which has sufficient productivity, which is easy to extract and, perhaps most importantly, which exhibits few antibiotic properties Over the past few years, national legislation has been introduced regulating the use of antibiotics in the feeding of animals intended for human consumption. Some countries have totally prohibited the use of antibiotics for animal feeds.

The present invention is a new compound of the elfamycin family, exhibiting little or no antibiotic effect but exhibiting an effect on animal growth of the same magnitude as the antibiotics previously described.

The compound of the present invention corresponds to the general formula:

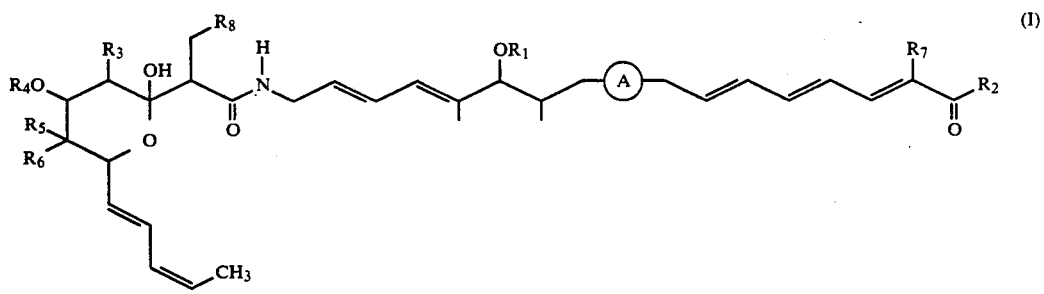

in which:
- the group $R_1$ represents an alkyl unit,
- the group $R_2$ represents a hydroxyl group or a substituted pyridone radical,
- the groups $R_3$, $R_5$, $R_6$ and $R_7$ represent either methyl or hydroxyl groups, or hydrogen, or alkyl groups,
- the group $R_4$ represents an alkyl group, hydrogen or a glycosidyl group,
- the group $R_8$ represents a hydrogen atom, a methyl group or an O(diginose)$_2$ group, and
- the group A represents a dihydroxyethanediyl link or a mono-or dihydroxyfuran ring in the 2,5-position of the furan ring, wherein $R_3$ represents a hydroxyl group and $R_6$ represents a methyl group.

More particularly the compound of the present invention corresponds to the formula (II):

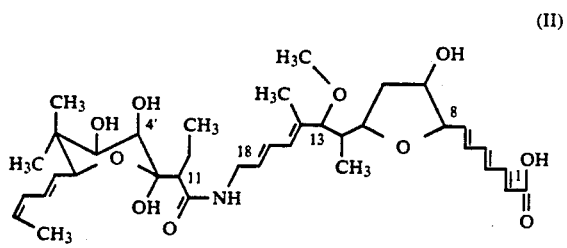

The compounds of the instant invention further include salts of the compound of the formula (II), for example, the alkali metal salts, preferably sodium or potassium, the alkaline earth metal salts, preferably calcium, and the salts of nitrogen compounds, preferably ammonium, triethylamine, lysine, arginine, etc.

The process for preparing the compounds according to the invention can be a fermentation process using a special strain of the Streptomyces genus deposited at the C.B.S. (Centraalbureau Voor Schimmelcultures, BAARN, HOLLAND) under the number CBS 473.89.

This strain of the Streptomyces genus may be used in the wild state or after it has undergone mutations, e.g. by means of radiation or chemical products well-known to those skilled in the art. When using this strain of the Streptomyces genus it is possible to produce only the single compound of formula (II).

This strain can be cultured in tubes, on an agar medium, containing:

| | |
|---|---|
| soluble starch: | 10 g/l |
| dipotassium phosphate: | 1 g/l |
| magnesium sulphate: | 1 g/l |

-continued

| | |
|---|---|
| sodium chloride: | 1 g/l |
| ammonium sulphate: | 2 g/l |
| calcium carbonate: | 2 g/l |
| traces of salt: | 1 g/l |
| agar: | 20 g/l |

This medium can be sterilized and is inoculated with the Streptomyces strain C.B.S. 473.89. The culture is maintained for 3 to 4 weeks at about 26° C.

In a second stage, an inoculum can be prepared in a 2-liter Erlenmeyer flask containing a culture medium containing:

| | |
|---|---|
| peptone: | 10 g/l |
| yeast extract: | 5 g/l |
| glucose: | 10 g/l |
| sodium chloride: | 5 g/l |
| agar: | 1.5 g/l |

This medium can be adjusted to a pH of about 7.4 and sterilized. It can be inoculated with an agar culture. Incubation can be performed at about 28° C. for approximately 72 hours.

This inoculum can be used to inoculate a 100 liter capacity fermenter containing 50 liters of the same medium as described above.

After about 48 hours of incubation at about 28° C. with stirring, a second, 800 liter fermenter containing 450 liters of the following culture medium can be inoculated from the first fermenter.

| | |
|---|---|
| distillers solubles: | 25 g/l |
| cerelose S.P.M.: | 10 g/l |
| soybean oil SIO: | 5 g/l |
| omyalite (calcium carbonate): | 5 g/l |
| ammonium sulphate: | 2 g/l |

The pH can be adjusted to about 7 with sodium hydroxide, and the medium can be sterilized and then inoculated with 50 liters of the above culture.

The incubation can last about 93 hours at about 26° C. with aeration and stirring. It is clear that the culture medium may be modified without departing from the scope of the present invention. Thus, any culture medium containing a carbon/hydrogen source, a nitrogen source and inorganic components, for example, phosphates, iron salts, cobalt, magnesium, calcium may be used within the scope of the present invention.

After fermentation, a medium containing 0.25 g/l of a product of formula (II) can be obtained.

Purification of the product of formula (II) can be carried out by passage through a series of columns packed with:

polystyrene-divinylbenzene resins (Duolite S861)
silica gel
polyamide resin.

Adsorption on DUOLITE resin can be carried out by contacting and evaporating an alcoholic, preferably methanolic, solution containing about 175 g of extract per liter of alcohol.

The product of formula (II) can be eluted with about an 80-90% methanol solution and isolated by evaporation of the alcohol.

The product obtained can thereafter be taken up in ethyl acetate and adsorbed on silica gel, then eluted with ethyl acetate from which it can be isolated by evaporation.

The final purification can be carried out by evaporation of a methanolic solution of the product in the presence of a polyamide resin, followed by an elution with a methanol/water solution of increasing methanol concentration. The methanol can be evaporated off, leaving an aqueous solution containing the product of formula (II).

The product of formula (II) can be useful for feeding animals, and preferably monogastric animals. It can be used, more preferably, for feeding piglets or poultry. The growth factor activity observed can be at least equal to that of the antibiotics currently used in this field, while the compound of the instant invention can exhibit practically or essentially no antibiotic effect.

The growth factor activity in the essential absence of antibiotic effect may be attributed to one or more of the stereoisomers of the compound of the formula (II).

The present invention will be described more completely by means of the following examples These example are in no case to be considered as limiting the invention.

EXAMPLE 1

1.1.—Strain

Reference: Streptomyces CBS 473.89
Storage: mixture of spores and sterile earth, dried under vacuum and kept at about +4° C. in the presence of actigel

1.2.—Culture on agar medium

Vessel: glass tube, L200 mm, diameter 24 mm, plugged with a cottonwool plug.
Filling: 22 ml

| Culture medium: | |
|---|---|
| soluble starch, DIFCO: | 10 g/l |
| dipotassium phosphate, PROLABO: | 1 g/l |
| magnesium sulphate, 7H$_2$O, PROLABO: | 1 g/l |
| sodium chloride, PROLABO: | 1 g/l |
| ammonium sulphate, PROLABO: | 2 g/l |
| calcium carbonate, PROLABO: | 2 g/l |
| agar, DIFCO: | 20 g/l |

The pH was not adjusted.
The culture medium was sterilized for about 20 minutes at about 122° C. During the cooling process following sterilization, the tubes were arranged in a slanting position.
Inoculation: with the earth-spore mixture (30 to 40 mg/tube). Incubation: 3-4 weeks at about 26° C.

1.3.—Inoculum culture (2-liter Erlenmeyer)

Vessel: 2-liter Erlenmeyer flask with 2 side tubes, one of which was equipped with an inoculation device. Closing with a polyurethane stopper.
Filling: 400 ml

| Culture medium: | |
|---|---|
| peptone, ORGANOTECHNIE: | 10 g/l |
| yeast extract, SPRINGER: | 5 g/l |
| glucose, PROLABO: | 10 g/l |
| sodium chloride, PROLABO: | 5 g/l |
| agar, PROLABO: | 1.5 g/l |

The pH was adjusted to 7.4 with 5 mls of 5N sodium hydroxide.
Sterilization: about 20 minutes at about 120° C.; after sterilization, the pH was 6.60.
Inoculation: with one agar culture for 2 flasks.
Incubation: about 72 hours at about 28° C. Shaker 150 rpm: stroke 5 cm.
The pH at the end of culturing was approximately 7.5.

1.4.—Inoculum culture (100-liter fermenter)

Vessel: stainless steel fermenter
Filling: 50 liters

| Culture medium: | |
|---|---|
| peptone, ORGANOTECHNIE: | 10 g/l |
| yeast extract, SPRINGER: | 5 g/l |
| cerelose: | 10 g/l |
| sodium chloride (purified fine salt no. 2, Salins du Midi): | 5 g/l |
| agar, PROLABO: | 2 g/l |
| pH before sterilization: | 7.2 |
| pH after sterilization: | 6.8 |
| Sterilisation: | about 40 minutes at about 122° C. |
| Inoculation: | with an Erlenmeyer inoculum culture (400 ml in 50 liters, i.e. 0.8%). |
| Incubation: | about 45 hours at about 28° C. |
| Stirring: | 300 rpm; aeration 5 m$^3$/h |

The pH at the end of culturing was approximately 7.9.
Antifoam consumed: 40 mls of EMKAPYL (polypropylene glycol) in the medium charged.

1.5.—Producer culture (800-liter fermenter)

Vessels: stainless steel fermenter equipped with 4 internal baffles
Filling: 450 liters

| Culture medium: | |
|---|---|
| distillers solubles, PRODULAC: | 25 g/l |
| cerelose (Societe des Produits du Mais): | 10 g/l |
| soybean oil: | 5 g/l |
| calcium carbonate: | 5 g/l |
| ammonium sulphate: | 2 g/l |

The pH before sterilization was about 7 with the addition of 450 mls of 10N NaOH.
The pH after sterilization was about 6.85.
Sterilization about 40 minutes at about 122° C.

| | |
|---|---|
| Inoculation: | 50 liters of the 100-liter fermenter inoculum culture (50 liters in 450 liters, i.e., a little more than 10%). |
| Incubation: | about 93 hours at about 26° C. |
| Stirring: | impeller rotating at 250 rpm |
| Aeration: | 15 m³/h at 0.8 bar |

The pH at the end of culturing was about 7.8. Antifoam consumed was 100 ml of EMKAPYL Concentration in the liquor obtained was 0.25 g/l of derivative of formula (II).

EXAMPLE 2—EXTRACTION

The pH of the fermentation liquor (2 500-liter fermenters, i.e. 1,000 liters of liquor in all) was adjusted to about 3 with 6N HCl.

500 liters of Ethyl acetate was added and the mixture was stirred for about 45 minutes, then centrifuged on a WESTFALIA NA7 centrifuge equipped for liquid/liquid/solid separation.

The ethyl acetate phase was evaporated to dryness under reduced pressure, leaving an oil, to which was added the residue, also oily, of a second extraction performed under the same conditions but using 200 liters of ethyl acetate.

This oil was taken up in 10 liters of methanol. 30 liters of Cyclohexane were added, the mixture was stirred and then allowed to settle. On evaporation of the phase richer in methanol, 700 g of a pulverulent solid were collected.

EXAMPLE 3—PURIFICATION

The 700 g of extract obtained in Example 2 were taken up in 4 liters of methanol. 4 liters of Duolite S861 resin were added, and the whole was evaporated to dryness under reduced pressure. The coated resin was then transferred to the top of a 15 cm diameter column containing a fresh 15 liter portion of the same resin. The fresh resin had been conditioned beforehand by washing with methanol followed by rinsing with demineralized water. The column was washed with 20 liters of 50% methanol and then 25 liters of 70% methanol.

The washing liquors were discarded. The column was then eluted, collecting 5-liter fractions, with 25 liters of 80% methanol followed by 60 liters of 90% methanol. A check by TLC showed that fractions 7 to 21 contained the desired product. On evaporation to dryness under reduced pressure, 372 g of the product were collected.

186 g or one half of this batch were taken up with 800 mls of ethyl acetate. 700 mls of Silica gel of porosity 60 A and particle size 40 to 63 μm (RHONE-POULENC LIMITED) were added to the solution obtained. The mixture was evaporated to dryness under reduced pressure and the pulverulent solid was loaded into a glass column 10 cm in diameter by 12 cm high. This column was connected to a column of the same diameter and filled 50 cm high with a fresh portion of the same silica. The column was eluted with pure ethyl acetate at a flow rate of 35 ml/min, collecting 500-ml fractions. A check by TLC showed that the desired product was contained in fractions 3 to 20 which, when combined and evaporated to dryness, gave a solid yield of 104 g.

100 g of this solid were taken and dissolved in 800 mls of methanol. 700 mls of polyamide resin (polycaprolactam or nylon 6) for chromatography, of a particle size of about 50 to 160 μm (MACHEREY-NAGEL) were added to the solution obtained. The whole was evaporated under reduced pressure, and the dry powder was loaded into a column 10 cm in diameter and 10 cm high. This column was fitted to the lower end of a column 8 cm in diameter and 50 cm high, filled with a fresh, dry portion of the same support.

The assembly was filled from bottom to top with 10% methanol to drive out the air, and was then eluted at a flow rate of 35 ml/min, collecting 500-ml fractions and applying a step gradient according to the following table:

| MeOH CONTENT | 500-ml FRACTION No. |
|---|---|
| 20% | 1 to 3 |
| 30% | 4 to 6 |
| 35% | 7 to 10 |
| 40% | 11 to 35 |
| 60% | 36 to 76 |

By thin-layer chromatography, the product was detected in fractions 41 to 70, which were combined. The methanol was evaporated off under reduced pressure and the residual aqueous phase (neutral pH) was extracted with ethyl acetate. On evaporation of the organic phase, an oil was obtained, which was diluted in 300 mls of methanol. This solution was poured very slowly into 8 liters of demineralized water with vigorous stirring. After drying in an oven under vacuum (40° C., 1 mm Hg) 61 g of the product of formula (II) were obtained.

PHYSICOCHEMICAL ANALYSIS

Calculated for $C_{37}H_{55}NO_{10}$: C %=65.95; H %=8.23; N %=2.08

Found: C %=64.26; H %=8.66; O %=2.00; $H_2O$=1.66% $[\alpha]^{20}_D$=+30.9+1 (C=0.5; methanol)

| WAVELENGTH MAX. nm | $E^{1\%}_{1\,cm}$ | ε |
|---|---|---|
| 289 | 538 | 36,200 |
| 233 | 762 | 51,200 |

TLC: chromatography on MERCK $F_{254}$ silica gel
layer thickness: 0.25 mm
ascending migration in:
1,2-dichloroethane    80 volumes
methanol    20 volumes
visualization: UV 254 nm and vanillin-sulphuric acid (dark blue)
$R_F = 0.35$ the structure of the product was confirmed by nuclear magnetic resonance at 400 megahertz in deuterated chloroform the infrared spectrum was recorded on an IR-Micolet 50 SxR spectrometer, in the form of KBr disks.

The characteristic bands of the spectrum were:

| | |
|---|---|
| 3425 cm$^{-1}$ | $\nu$ OH + $\nu$ NH |
| 3020 cm$^{-1}$ | $\nu$ CH (trans olefin) |
| 2970 cm$^{-1}$ | $\nu_{as}$ CH$_3$ |
| 2930 cm$^{-1}$ | $\nu_{as}$ CH$_2$ |
| 2875 cm$^{-1}$ | $\nu_s$ CH$_3$ |
| 2820 cm$^{-1}$ | $\nu_s$ CH$_2$ |
| 3000–2450 cm$^{-1}$ | $\nu$ OH (acid) |
| 1690 cm$^{-1}$ | $\nu$ C = O (acid) |
| 1637 | $\nu$ C = C |
| 1620 cm$^{-1}$ | $\nu$ C = O (amide) |
| 1545 cm$^{-1}$ | $\delta$ NH |
| 1460; 1445 cm$^{-1}$ | $\delta$ CH$_2$ + $\delta_{as}$CH$_3$ |
| 1410 cm$^{-1}$ | $\delta$ OH |

| -continued | |
|---|---|
| 1380 cm$^{-1}$ | $\delta_s CH_3$ |
| 1255 cm$^{-1}$ | $\upsilon$ C—O (acid) |
| 1095-1005 cm$^{-1}$ | $\upsilon$ C—O (ether + alcohol) |
| 980 cm$^{-1}$ | W CH (trans CH=CH) |
| 935 cm$^{-1}$ | |

EXAMPLE 4

Antibacterial Activity of the Compound of Formula (II)

Description of the test method used

The strains used, identified in the following table, were thawed at the time of use and then diluted to obtain the following concentrations:

$10^7$ bacteria/ml for the aerobic bacteria
$10^6$ bacteria/ml for the anaerobic bacteria.

A stock suspension of the product of formula (II) was prepared at a concentration of 3000 mg/l in water. It was then diluted with water to obtain concentrations of 300 mg/l, 100 mg/l, 50 mg/l and 25 mg/l.

The culture media were the following:
Mueller Hinton Agar (MHA) for the aerobic cultures
Mueller Hinton Agar (MHA)+2% Fildes (MHA) for the anaerobic cultures.

Procedure

Each dilution of product was added to 20 mls of the culture medium maintained supercooled at 45° C., and the medium was then poured into Petri dishes. After gentle agitation, the dishes were dried open for about 1 hour at about 37° C.

Inoculation was carried out with a DENLEY multipoint inoculator, which deposited $10^{-3}$ ml of each inoculum per spot.

Reading was performed after about 18 hours of incubation at about 37° C. for the aerobes and about 48 hours at about 37° C. for the anaerobes.

The minimal inhibitory concentration (MIC) was the lowest concentration for which no growth was observed.

| ANTIBACTERIAL ACTIVITY OF THE PRODUCT OF FORMULA (II) | |
|---|---|
| AEROBIC STRAINS | MIC in mg/l |
| *Staphylococcus aureus* 209P | inactive at 300 |
| *Staphylococcus aureus* S t$_A$ 1 | inactive at 300 |
| *Staphylococcus aureus* S t$_A$ 2 | inactive at 300 |
| *Staphylococcus aureus* Weichbrodt | inactive at 300 |
| *Staphylococcus epidermis* | inactive at 300 |
| *Staphylococcus faecalis* | inactive at 300 |
| *Streptococcus bovis* 3 | inactive at 300 |
| *Streptococcus bovis* 5 | 25 |
| *Streptococcus uberis* 3 | 50 |
| *Streptococcus uberis* 8 | 100 |
| *Escherichia coli* INRA ECi | inactive at 300 |
| *Escherichia coli* DCO | inactive at 300 |
| *Escherichia coli* DC2 | 100 |
| *Klebsiella pneumoniae* Caroli | inactive at 300 |
| *Enterobacter cloacae* IP 085 | inactive at 300 |
| *Pseudomonas aeruginosa* IP A 237 | inactive at 300 |
| *Pasterella multocida* IP | inactive at 300 |
| *Proteus vulgaris* IP A272 | inactive at 300 |
| *Proteus mirabilis* Villette | inactive at 300 |
| *Clostridium perfringens* IP 615 | inactive at 100 |
| *Clostridium perfringens* ATCC 13124 | inactive at 100 |
| *Clostridium septicum* | inactive at 100 |
| *Bacteroides fragilis* ATCC 25285 | inactive at 100 |
| *Bacteroides fragilis* 479R | inactive at 100 |
| *Bacteroides thetaiotaomicron* ATCC 29741 | inactive at 100 |
| *Bacteroides melaninogenicus* ATCC 15930 | inactive at 100 |

EXAMPLE 5

Use of the product of formula II as a growth factor

This experiment compared the efficacy of the product of the formula II in weaned piglets, to that of two commonly used growth factors: spiramycin embonate (SPIRA 200, RHONE-POULENC) and tylosin (TYLAN 20, ELANCO).

Experimental design

The experiment compared 5 treatments corresponding to the distribution of a control piglet feed (feed+amino acids) or of the same mixture supplemented with 40 ppm spiramycin which was comparative test 1, with 40 ppm tylosin which was comparative test 2, or with 40 and 60 ppm of a compound of formula II which were tests 1 and 2.

TABLE 1

| Percentage composition and characteristics of the diets | | | | | |
|---|---|---|---|---|---|
| | Control | Compa 1 | Compa 2 | Test 1 | Test 2 |
| Maize | 35 | 35 | 35 | 35 | 35 |
| Cassava | 15 | 15 | 15 | 15 | 15 |
| Soya cake | 22.7 | 22.7 | 22.7 | 22.7 | 22.7 |
| Sugar | 2 | 2 | 2 | 2 | 2 |
| Tallow | 1.7 | 1.7 | 1.7 | 1.7 | 1.7 |
| Fine bran | 10 | 10 | 10 | 10 | 10 |
| Peas | 8.6 | 8.6 | 8.6 | 8.6 | 8.6 |
| C.M.V. | 4 | 4 | 4 | 4 | 4 |
| Control premix | 1 | — | — | — | — |
| Comp. premix 1 | — | 1 | — | — | — |
| Comp. premix 2 | — | — | 1 | — | — |
| Test premix 1 | — | — | — | 1 | — |
| Test premix 2 | — | — | — | — | 1 |
| CHARACTERISTIC CALCULATED | | | | | |
| Digestible energy (Kal/kg) | 3,200 | 3,200 | 3,200 | 3,200 | 3,200 |
| CHARACTERISTICS ANALYZED | | | | | |
| Nitrogenous matter % | 18.00 | | | | |
| Lysine % | 1.14 | | | | |

TABLE 2

| Percentage composition of the C.M.V. | |
|---|---|
| Dicalcium phosphate | 37.50 |
| Calcium carbonate | 30.00 |
| Salt (NaCl) | 10.00 |
| Pig trace elements 3042/Se | 1.90 |
| Choline concentrate, 50% | 3.00 |
| Pig ADEB complex 188 | 0.50 |
| Carrier | 17.10 |

TABLE 3

| Percentage composition of the premixes | | | | | |
|---|---|---|---|---|---|
| | Control | Compa 1 | Compa 2 | Test 1 | Test 2 |
| DL-Methionine | 11 | 11 | 11 | 11 | 11 |
| L-Lysine | 20 | 20 | 20 | 20 | 20 |
| L-Threonine | 4 | 4 | 4 | 4 | 4 |
| Spira 200 | — | 2 | — | — | — |
| Tylan 20 | — | — | 20 | — | — |

TABLE 3-continued

| Percentage composition of the premixes | | | | | |
|---|---|---|---|---|---|
| | Control | Compa 1 | Compa 2 | Test 1 | Test 2 |
| Formula (II) | — | — | — | 0.4 | 0.6 |
| Maize starch q.s. 100 | 65 | 63 | 45 | 64.6 | 64.4 |

Animals 130 weaned Large-White Belgian Landrace crossed piglets were used. The experiment began 2 weeks after weaning of the animals, i.e. at a mean age of 42 days. The piglets, of a mean weight of 10.7 kg, were distributed in 13 groups of 5 pairs of animals of the same weight.

Condition of granulation of the piglet feed

The batch of feed was granulated on a KAHL 400 type granulating press equipped with a stainless steel die of a 35 mm compressing thickness with holes 2.5 mm in diameter.

Before compression, the meal was conditioned with steam at saturation at 0.5 bar on a continuous kneader.

The temperatures noted were about 56° C. for the meal and about 66° C. for the granules as they emerged from the die.

The parameters noted on the press were 65 A (12 kw) at the principal motor, and the rate of output of granule is 700 kg/h.

Cooling was provided in a static vertical cooler for approximately 15 min.

The hardness of the cooled granules, measured in a Kajl apparatus after 72 h, was 10 kg.

Feeding

The animals received the experimental feed ad libitum in the form of granules 2.5 mm in diameter. The percentage composition and the characteristics of the diets are shown in Table 1. Table 2 shows the composition of the Compose Mineral et Vitaminique (C.M.V.) (Mineral and Vitamin Compound) and Table 3 shows the composition of the premixes of additives.

Monitoring

The animals were weighed at the beginning, middle and end of the experiment. The consumptions were noted every week.

Results

The results of consumption, growth and nutritional efficacy are shown in Table 4 for the period 0-14 days, in Table 5 for the period 14-28 days and in Table 6 for the period 0-28 days.

TABLE 4

| Performance of the animals during the period 0-14 days | | | | | |
|---|---|---|---|---|---|
| | Control | Compa 1 | Compa 2 | Test 1 | Test 2 |
| Initial weight (kg) | 10.7 | 10.8 | 10.7 | 10.8 | 10.2 |
| Consumption (g/day) | 614 | 668 | 619 | 625 | 599 |
| Weight gain (g/day) | 329 | 393 | 351 | 360 | 338 |
| Index of consumption | 1.88 | 1.72 | 1.79 | 1.77 | 1.78 |
| Intermediate Weight (kg) | 15.3 | 16.3 | 15.6 | 15.8 | 15.3 |

TABLE 5

| Performance of the animals during the period 14-28 days | | | | | |
|---|---|---|---|---|---|
| | Control | Compa 1 | Compa 2 | Test 1 | Test 2 |
| Initial weight (kg) | 15.3 | 16.3 | 15.6 | 15.8 | 15.3 |
| Consumption (g/day) | 1031 | 1147 | 1033 | 1068 | 1026 |
| Weight gain (g/day) | 560 | 647 | 588 | 620 | 588 |
| Index of consumption | 1.86 | 1.79 | 1.76 | 1.73 | 1.74 |
| Intermediate Weight (kg) | 23.1 | 25.4 | 23.8 | 24.5 | 23.5 |

TABLE 6

| Performance of the animals during the period 0-28 days | | | | | |
|---|---|---|---|---|---|
| | Control | Compa 1 | Compa 2 | Test 1 | Test 2 |
| Initial weight (kg) | 10.7 | 10.8 | 10.7 | 10.8 | 10.6 |
| Consumption (g/day) | 822 | 908 | 826 | 847 | 812 |
| Weight gain (g/day) | 445 | 518 | 470 | 490 | 463 |
| Index of consumption | 1.85 | 1.75 | 1.76 | 1.73 | 1.75 |
| Intermediate Weight (kg) | 23.1 | 25.4 | 23.8 | 24.5 | 23.5 |

During the first period, tendencies were already noted which were subsequently confirmed, i.e., an increase in consumption of the animals receiving the diet supplemented with spiramycin and a decrease in the index of consumption (consumption/weight gain ratio) of the animals receiving the diets supplemented with the growth factors.

During the second period (14-28 days), a significant difference was observed between diets for the criterion "consumption".

The growth of the animals was significantly improved by the addition of spiramycin to the basic diet, and was improved in the same way by the addition of the other growth factors.

The overall period (0-28 days) was the most interesting. Since it was longer, it enabled the significant effects to be detected more readily. Consumption and growth were, during that period, significantly increased by the addition of spiramycin to the basic diet.

The product II at 40 ppm brought about an improvement in growth of 10% relative to the basic diet. The performances of the animals fed with the diet containing the product II at 60 ppm are somewhat behind those observed with the same product at 40 ppm. The index of consumption was significantly improved irrespective of the growth factor and irrespective of the dose in question.

Under the conditions of our experiment, considering the overall period:

the product II improved quite significantly the index of consumption of the animals. This improvement was comparable to that observed with spiramycin and tylosin.

the product II, in contrast to spiramycin, did not bring about a significant improvement in consumption.

As to increased consumption, the product was comparable to tylosin.

EXAMPLE 6

Example 5 was repeated using the product of formula II as a growth factor at doses of 10, 20 and 40 ppm (tests 3, 4 and 5), in comparison with spiramycin used at a dose of 40 ppm. Tables 7, 8 and 9 respectively show the percentage composition and the characteristics of the diets, the percentage composition of the CMV and the percentage composition of the premixes.

TABLE 7

Percentage composition and characteristics of the diets

|  | C | TEST 3 | TEST 4 | TEST 5 | SPIRA |
|---|---|---|---|---|---|
| Maize |  | 3.3 | 3.3 | 3.3 | 3.3 |
| Barley |  | 28.2 | 28.2 | 28.2 | 28.2 |
| Fine bran |  | 9.1 | 9.1 | 9.1 | 9.1 |
| Tallow |  | 2.8 | 2.8 | 2.8 | 2.8 |
| Maize oil |  | 1.0 | 1.0 | 1.0 | 1.0 |
| Cassava |  | 15.0 | 15.0 | 15.0 | 15.0 |
| Sugar |  | 2.0 | 2.0 | 2.0 | 2.0 |
| Soya cake 48 |  | 21.1 | 21.1 | 21.1 | 21.1 |
| Peas |  | 10.0 | 10.0 | 10.0 | 10.0 |
| Fish meal 70 |  | 2.5 | 2.5 | 2.5 | 2.5 |
| C.M.V. |  | 4.0 | 4.0 | 4.0 | 4.0 |
| Control premix | 1 | — | — | — | — |
| Test premix 3 | — | 1 | — | — | — |
| Test premix 4 | — | — | 1 | — | — |
| Test premix 5 | — | 1 | — | 1 | — |
| Spira premix | — | — | — | — | 1 |
| CHARACTERISTIC CALCULATED |  |  |  |  |  |
| Net energy (kcal/kg) % |  |  | 2,320 |  |  |
| Crude protein % |  |  | 19.00 |  |  |
| Total lysine % |  |  | 1.19 |  |  |
| Digestible lysine % |  |  | 1.03 |  |  |

TABLE 8

Percentage composition of the C.M.V.

| Dicalcium phosphate | 35.75 |
|---|---|
| Calcium carbonate | 25.00 |
| Salt (NaCl) | 10.00 |
| Trace elements (new formula) | 2.00 |
| Piglet ADEB complex (new fla.) | 1.00 |
| Choline concentrate, 50% | 3.75 |
| Carrier (starch) | 22.50 |

TABLE 9

Percentage composition of the premixes

|  | Control | TEST 3 | TEST 4 | TEST 5 | SPIRA |
|---|---|---|---|---|---|
| DL-Methionine | 12.7 | 12.7 | 12.7 | 12.7 | 12.7 |
| L-Lysine HCl | 11.7 | 11.7 | 11.7 | 11.7 | 11.7 |
| L-Threonine | 3.1 | 3.1 | 3.1 | 3.1 | 3.1 |
| L-Tryptophan | 1.0 | 1.0 | 1.0 | 1.0 | 1.0 |
| Compound of formula (II) 90% | — | 0.11 | 0.22 | 0.44 | — |
| Spiramycin | — | — | — | — | 2.0 |
| Maize starch | 71.5 | 71.39 | 71.28 | 71.06 | 69.5 |

The experiment protocol, granulation condition, animals, feeding and monitoring were the same as in Examples 1-3 and 5.

The results are shown in Table 10 for the period 0-14 days, Table 11 for the period 14-28 days and Table 12 for the period 0-28 days.

TABLE 10

Performance of the animals during the period 0-14 days

|  | C | TEST 3 | TEST 4 | TEST 5 | SPIRA |
|---|---|---|---|---|---|
| Initial weight (kg) | 11.5 | 11.5 | 11.5 | 11.5 | 11.4 |
| Consumption (g/d) | 645 | 694 | 689 | 701 | 715 |
| Weight gain (g/d) | 368 | 418 | 430 | 416 | 423 |
| Index of consumption | 1.76 | 1.70 | 1.61 | 1.70 | 1.70 |

TABLE 11

Performances of the animals during the period 14-28 days

|  | C | TEST 3 | TEST 4 | TEST 5 | SPIRA |
|---|---|---|---|---|---|
| Consumption (g/d) | 1059 | 1133 | 1164 | 1099 | 1130 |
| Weight gain (g/d) | 579 | 648 | 664 | 648 | 640 |
| Index of consumption | 1.84 | 1.75 | 1.75 | 1.70 | 1.77 |
| Final weight (kg) | 24.7 | 26.4 | 26.8 | 26.4 | 26.3 |

TABLE 12

Performances of the animals during the period 0-28 days

|  | C | TEST 3 | TEST 4 | TEST 5 | SPIRA |
|---|---|---|---|---|---|
| Initial weight (kg) | 11.5 | 11.5 | 11.5 | 11.5 | 11.4 |
| Consumption (g/d) | 852 | 914 | 927 | 900 | 923 |
| Weight gain (g/d) | 474 | 533 | 547 | 532 | 532 |
| Index of consumption | 1.80 | 1.72 | 1.69 | 1.70 | 1.73 |
| Final weight (kg) | 24.7 | 26.4 | 26.8 | 26.4 | 26.3 |

We claim:

1. A compound selected from the group consisting of an acid represented by formula (II)

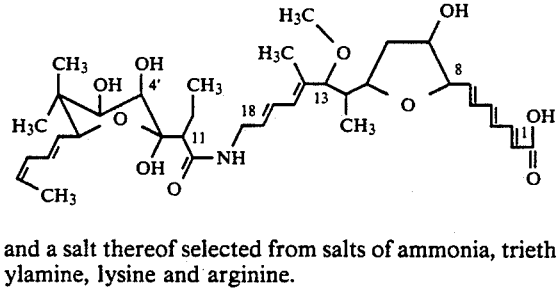

and a salt thereof selected from salts of ammonia, triethylamine, lysine and arginine.

2. A composition of matter having substantially no antibiotic effect comprising an animal feed and a compound selected from the group consisting of an acid represented by formula (II)

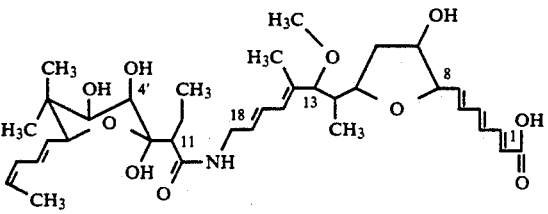

and a salt thereof.

3. A composition of matter comprising the compound of claim 1 and an animal feed.

* * * * *